US008765366B2

(12) United States Patent
Lalvani et al.

(10) Patent No.: US 8,765,366 B2
(45) Date of Patent: Jul. 1, 2014

(54) CLINICAL CORRELATES

(75) Inventors: Ajit Lalvani, Oxford (GB); Kerry Millington, London (GB)

(73) Assignee: Ajit Lalvani, Oxford (GB)

(*) Notice: Subject to any disclaimer, the term of this patent is extended or adjusted under 35 U.S.C. 154(b) by 20 days.

(21) Appl. No.: 12/293,249

(22) PCT Filed: Mar. 16, 2007

(86) PCT No.: PCT/GB2007/000934
§ 371 (c)(1),
(2), (4) Date: Feb. 4, 2009

(87) PCT Pub. No.: WO2007/107714
PCT Pub. Date: Sep. 27, 2007

(65) Prior Publication Data
US 2009/0170120 A1 Jul. 2, 2009

(30) Foreign Application Priority Data

Mar. 17, 2006 (GB) .................................. 0605474.6

(51) Int. Cl.
*A61K 39/04* (2006.01)
*C12Q 1/00* (2006.01)
*C12Q 1/68* (2006.01)

(52) U.S. Cl.
USPC ...... 435/4; 424/184.1; 424/234.1; 424/248.1; 435/6.15

(58) Field of Classification Search
None
See application file for complete search history.

(56) References Cited

U.S. PATENT DOCUMENTS 6,218,132 B1 4/2001 Spack et al.
2002/0032162 A1 3/2002 Content et al.

FOREIGN PATENT DOCUMENTS

WO WO 98/23960 * 6/1998
WO WO 02/054072 7/2002

OTHER PUBLICATIONS

Emu B., et al (Journal of Virology 79(22):2005:pp. 14169-14178).*
Bourgarit et al (AIDS, Jan. 2006, Vo. 20, No. 2, pp. F1-F7).*
Delgado et al (PNAS, vol. 99, No. 11, May 28, 2002, p. 7576-7581).*
Greenspan et al. (Nature Biotechnology 7: 936-937, 1999).*
Bowie et al (Science, 1990, 257:1306-1310).*
Magnani et al (Clin Exp Immunol 2000, 119:99-106).*
Mori et al (American Journal of Respiratory and Critical Care Medicine, vol. 170, 2004, pp. 59-64).*
Boaz et al., "Presence of HIV-1 Gag-specific IFN-gamma+IL-2+ and CD28+IL-2+ CD4 T cell responses is associated with nonprogression in HIV-1 infection," J Immunol. Dec. 1, 2002;169(11):6376-85.

Bourgarit et al., "Explosion of tuberculin-specific Th1-responses induces immune restoration syndrome in tuberculosis and HIV co-infected patients." AIDS (London, England) Jan. 9, 2006, vol. 20, No. 2, Jan. 9, 2006, pp. F1-F7.
Delgado et al., "Antigen-specific and persistent tuberculin anergy in a cohort of pulmonary tuberculosis patients from rural Cambodia." Proceedings of the National Academy of Sciences of the United States of America May 28, 2002, vol. 99, No. 11, May 28, 2002, pp. 7576-7581.
Emu et al., "Phenotypic, functional, and kinetic parameters associated with apparent T-cell control of human immunodeficiency virus replication in individuals with and without antiretroviral treatment" Journal of Virology Nov. 2005, vol. 79, No. 22, Nov. 2005, pp. 14169-14178.
Ewer et al., "Comparison of T-cell-based assay with tuberculin skin test for diagnosis of Mycobacterium tuberculosis infection in a school tuberculosis outbreak" Lancet The, Lancet Limited. London, GB, vol. 361, No. 9364, Apr. 5, 2003, pp. 1168-1173.
Fuller et al., "Ablation of CD8 and CD4 T cell responses by high viral loads," J Immunol. Jan. 1, 2003;170(1):477-86.
Guyot-Revol et al., "Regulatory T cells are expanded in blood and disease sites in patients with tuberculosis." American Journal of Respiratory and Critical Care Medicine Apr. 1, 2006, vol. 173, No. 7, Dec. 9, 2005, pp. 803-810.
Harari et al., "Functional heterogeneity of memory CD4 T cell responses in different conditions of antigen exposure and persistence." Journal of Immunology (Baltimore, MD. : 1950) Jan. 15, 2005, vol. 174, No. 2, Jan. 15, 2005, pp. 1037-1045.
Harari et al., "Skewed representation of functionally distinct populations of virus-specific CD4 T cells in HIV-1-infected subjects with progressive disease: changes after antiretroviral therapy," Blood. Feb. 1, 2004;103(3):966-72. Epub Sep. 4, 2003.
Howe et al., "Functional heterogeneity among CD4+ T-cell clones from blood and skin lesions of leprosy patients. Identification of T-cell clones distinct from Th0, Th1 and Th2," Immunology. Apr. 1995;84(4):585-94.
International Preliminary Report on Patentability issued Sep. 23, 2008 during the prosecution of International Application No. PCT/GB2007/000934. Published Sep. 23, 2008.
International Search Report issued Sep. 11, 2007 during the prosecution of International Application No. PCT/GB2007/000934. Published Nov. 15, 2007.
Lucas et al., "Ex vivo phenotype and frequency of influenza virus-specific CD4 memory T cells," J Virol. Jul. 2004;78(13):7284-7.
Magnani et al., "Circulating, Mycobacterium tuberculosis-specific lymphocytes from PPD skin test-negative patients with tuberculosis do not secrete interferon-gamma (IFN-gamma) and lack the cutaneous lymphocyte antigen skin-selective homing receptor," Clin Exp Immunol. Jan. 2000;119(1):99-106.
Millington et al., "Dynamic relationship between IFN-gamma and IL-2 profile of Mycobacterium tuberculosis-specific T cells and antigen load." Journal of Immunology (Baltimore, MD. : 1950) Apr. 15, 2007, vol. 178, No. 8, Apr. 15, 2007, pp. 5217-5226.

(Continued)

Primary Examiner — Rodney P Swartz
(74) Attorney, Agent, or Firm — Fulbright & Jaworski LLP

(57) ABSTRACT

A method of assessing an intracellular pathogen infection and/or monitoring an intracellular pathogen infection in an individual comprises determining whether the individual has (a) T-cells that secrete IFN-γ only, (b) T-cells that secrete IL-2 only or (c) T-cells that secrete both IFN-γ and IL-2 in response to an intracellular pathogen antigen and optionally determining any change in this cytokine profile.

18 Claims, 14 Drawing Sheets

(56) References Cited

OTHER PUBLICATIONS

Semmo et al., "Preferential loss of IL-2-secreting CD4+ T helper cells in chronic HCV infection." Hepatology (Baltimore, MD.) May 2005, vol. 41, No. 5, May 2005, pp. 1019-1028.

Sommer et al., "Analysis of cytokine patterns produced by individual CD4+ lymph node cells during experimental murine leishmaniasis in resistant and susceptible mice," Int Immunol. Dec. 1998;10(12):1853-61.

Sun et al., "Dysfunction of simian immunodeficiency virus/simian human immunodeficiency virus-induced IL-2 expression by central memory CD4+ T lymphocytes," J Immunol. Apr. 15, 2005;174(8):4753-60.

Tsukaguchi et al., "CD4+ alpha beta T cell and gamma delta T cell responses to Mycobacterium tuberculosis. Similarities and differences in Ag recognition, cytotoxic effector function, and cytokine production." Journal of Immunology (Baltimore, MD. 1950) Feb. 15, 1995, vol. 154, No. 4, Feb. 15, 1995, pp. 1786-1796.

United Kingdom Search Report issued Jul. 10, 2006 during the prosecution of Application No. GB0605474.6.

Written Opinion issued Sep. 11, 2007 during the prosecution of International Application No. PCT/GB2007/000934. Published Sep. 17, 2008.

Younes et al., "HIV-1 viremia prevents the establishment of interleukin 2-producing HIV-specific memory CD4+ T cells endowed with proliferative capacity," J Exp Med. Dec. 15, 2003;198(12):1909-22.

Eun-Kyeong Jo, et al.; "Dynamics of cytokine generation in patients with active pulmonary tuberculosis"; Current Opinion in Infectious Diseases; 2003; vol. 16; pp. 205-210.

European Examination Report, issued Aug. 12, 2009 (published Aug. 12, 2009) during the prosecution of European Application No. 07712923.7.

Arend et al., "Antigenic equivalence of human T-cell responses to *Mycobacterium tuberculosis*-specific RD1-encoded protein antigens ESAT-6 and culture filtrate protein 10 and to mixtures of synthetic peptides," *Infection and Immunity*, 68(6):3314-3321, 2000.

Jones et al., "Degeneracy of T cell receptor recognition of an influenza virus hemagglutinin epitope restricted by HLA-DQ and -DR class II molecules," *Eur. J. Immunol.*, 24:1137-1142, 1994.

Mustafa et al., "Immunogenicity of *Mycobacterium tuberculosis* RD1 region gene products in infected cattle," *Clin Exp Immunol*, 130:37-42, 2002.

Okkels et al., "PPE protein (Rv3873) from DNA segment RD1 of *Mycobacterium tuberculosis*: strong recognition of both specific T-cell epitopes and epitopes conserved within the PPE family," *Infection and Immunity*, 71(11):6116-6123, 2003.

Shirai et al., "Induction of cytotoxic T cells to a cross-reactive epitope in the hepatitis C virus nonstructural RNA polymerase-like protein," *Journal of Virology*, 66(7):4098-4103, 1992.

Van der Zee et al., "Efficient mapping and characterization of a T cell epitope by the simultaneous synthesis of multiple peptides," *Eur. J. Immunol.*, 19:43-47, 1989.

Office Action issued in European Application No. 07 712 923.7, mailed Jun. 1, 2011.

Caccamo, Nadia, et al.; "Multifunctional CD4" T Cells Correlate with Active Mycobacterium Tuberculosis Infection; Eur. J. Immunol., 2010, vol. 40, pp. 221-2220.

Casey, Rosalyn, et al.; "Enumeration of Functional T-Cell Subsets by Fluorescence-Immunospot Defines Signatures of Pathogen Burden in Tuberculosis"; PloS One. Dec. 2010, vol. 5, Issue 12, pp. 1-11.

Sester, Urban, et al.; "Whole-Blook Flow-Cytometric Analysis of Antigen-Specific CD4 T-Cell Cytokine Profiles Distinguishes Active Tuberculosis from Non-Active States": Plos One, Mar. 2011, vol. 6, issue 3. e17813, pp. 1-7.

\* cited by examiner

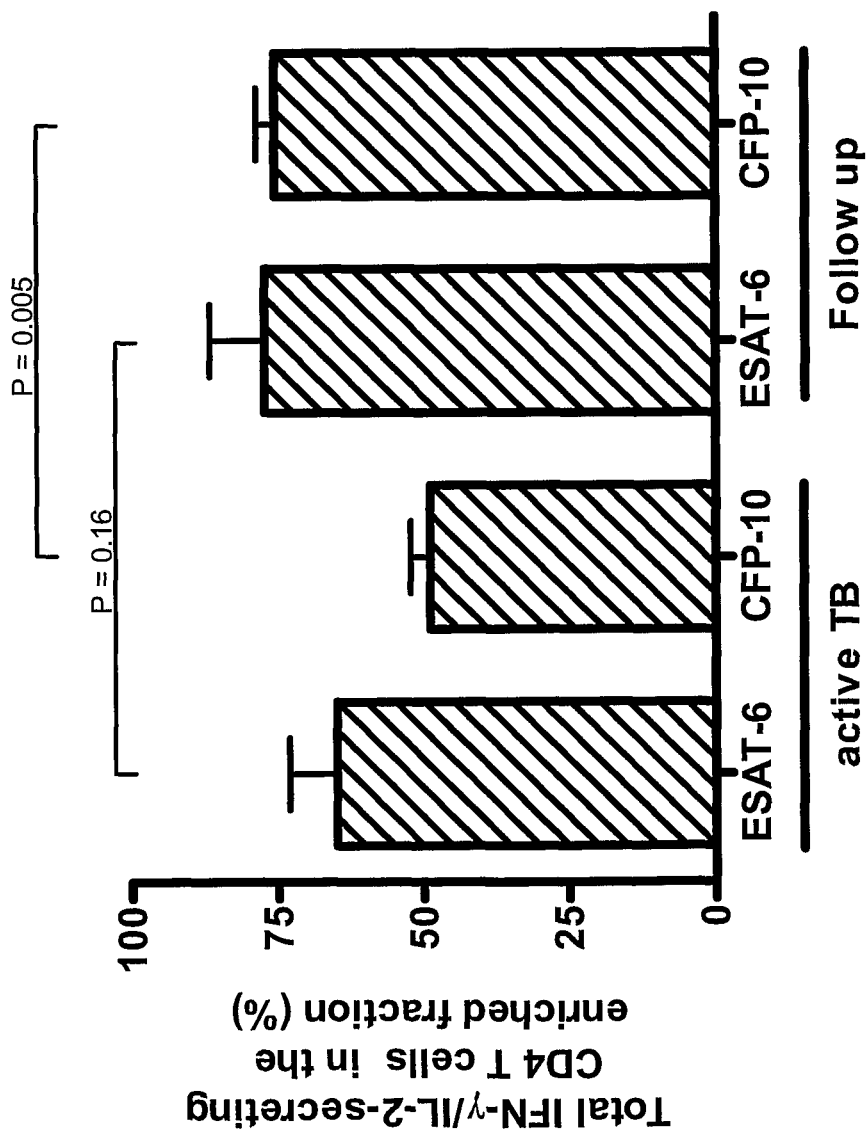
Figure 2A(ii)

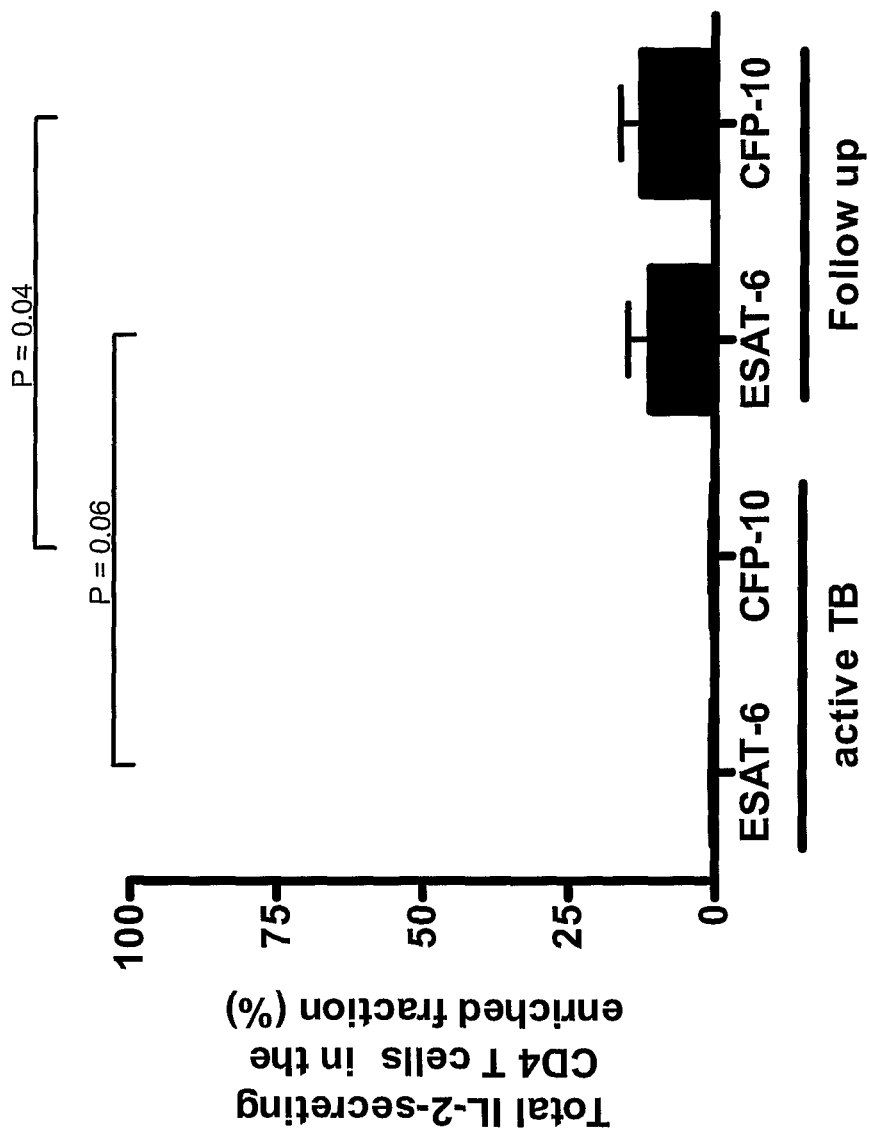
Figure 2A(iii)

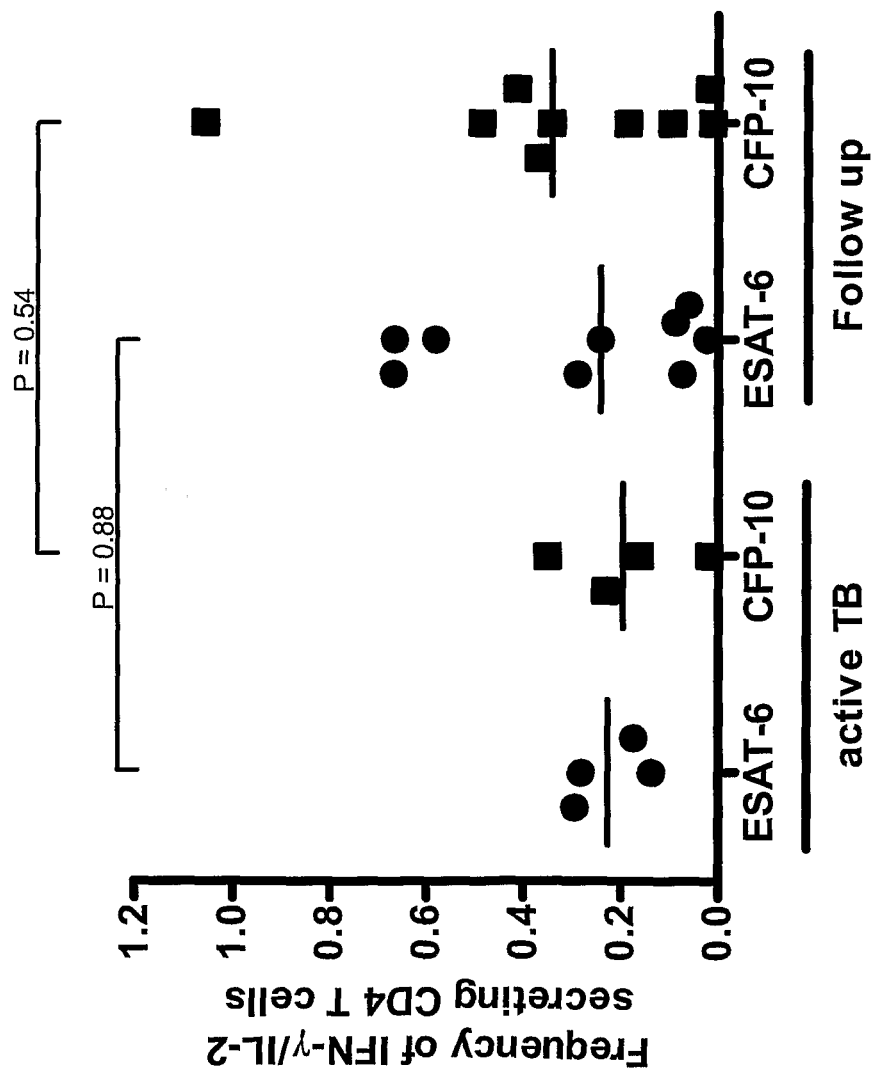
Figure 2B(ii)

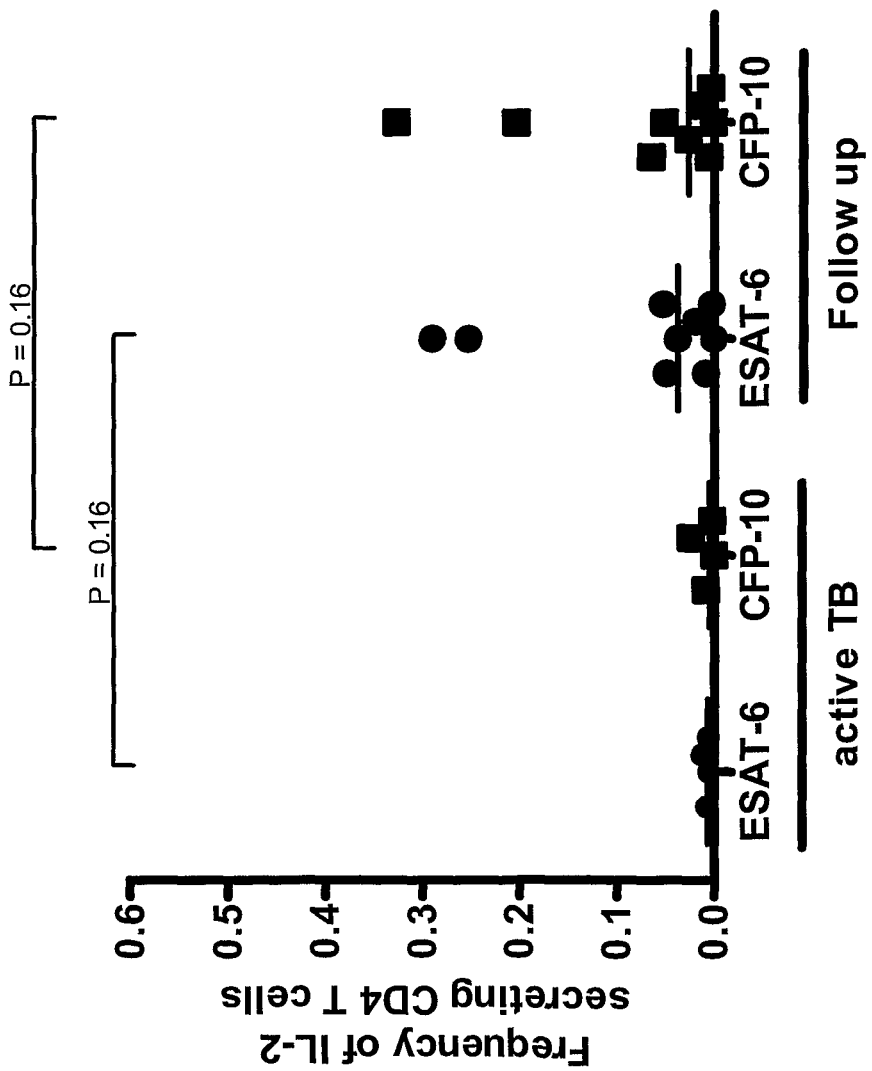
Figure 2B(iii)

SEQUENCE LISTING

<160> NUMBER OF SEQ ID NOS: 2

<210> SEQ ID NO 1
<211> LENGTH: 95
<212> TYPE: PRT
<213> ORGANISM: Mycobacterium tuberculosis

<400> SEQUENCE: 1

Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95

<210> SEQ ID NO 2
<211> LENGTH: 100
<212> TYPE: PRT
<213> ORGANISM: Mycobacterium tuberculosis

<400> SEQUENCE: 2

Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
            20                  25                  30

Glu Ser Thr Ala Gly Ser Leu Gln Gly Gln Trp Arg Gly Ala Ala Gly
        35                  40                  45

Thr Ala Ala Gln Ala Ala Val Val Arg Phe Gln Glu Ala Ala Asn Lys
    50                  55                  60

Gln Lys Gln Glu Leu Asp Glu Ile Ser Thr Asn Ile Arg Gln Ala Gly
65                  70                  75                  80

Val Gln Tyr Ser Arg Ala Asp Glu Glu Gln Gln Gln Ala Leu Ser Ser
                85                  90                  95

Gln Met Gly Phe
            100

CLINICAL CORRELATES

This application is a national phase application under 35 U.S.C. §371 of International Application No. PCT/GB2007/000934 filed Mar. 16, 2007, which claims priority to Great Britain Patent Application No. GB 0605474.6 filed Mar. 17, 2006. The entire text of each of the above-referenced disclosures is specifically incorporated herein by reference without disclaimer.

FIELD OF THE INVENTION

The present invention relates methods of monitoring mycobacterial infections, such as *Mycobacterium tuberculosis* infection and kits for use in such methods.

BACKGROUND TO THE INVENTION

There is a need for markers of infection status of an individual. Use of such markers allows treatment, prevention and control of the relevant disease. For example, monitoring the status of an individual infected with tuberculosis (TB) is essential for the treatment, prevention and control of this resurgent disease. Mycobacterial load cannot be measured directly and there is currently no biomarker reflecting mycobacterial load. In addition, *Mycobacterium tuberculosis* is often difficult to culture from patients with active TB, and impossible to culture from healthy latently infected people. Therefore an immune-based diagnostic test indicating the status of the *Mycobacterium tuberculosis* infection would be very useful in a number of clinical scenarios guiding the treatment, prevention and control of this infection. For example, differentiating between active and latent infection, monitoring efficacy of anti-tuberculosis therapy of active and latent TB, monitoring efficacy of therapeutic vaccines and new drugs and detecting early progression to active disease.

Mycobacterial antigens are known in the art. For example, early secretory antigen target-6 (ESAT-6) and culture filtrate protein 10 (CFP-10) are two *Mycobacterium tuberculosis* antigens that have been intensively investigated in animal models and humans over the last few years. ESAT-6 and CFP-10 are strong targets of 25 the cellular immune response in animal models, tuberculosis patients and contacts and so may be used in specific T cell-based blood tests.

SUMMARY OF THE INVENTION

The present inventors have shown that the profile of T-cell-derived IFN-γ and IL-2 secretion correlates with different clinical outcomes of intracellular pathogen infection. The invention thus provides an indirect immunological biomarker of intracellular pathogen load and status in vivo which can be used to predict, determine and monitor clinical outcome as well as monitor the effect of therapeutic or vaccine intervention on infection.

More particularly, the inventors have shown that the IFN-γ/IL-2 cytokine profile of pathogen antigen-specific CD4 T-cells changes in relation to antigen load. During states of high antigen load antigen-specific CD4 T-cells secrete IFN-γ only and IFN-γ/IL-2. During states of low antigen load antigen-specific T-cells stop secreting IFN-γ only, predominantly secrete IFN-γ/IL-2 and newly secrete IL-2 only. This cytokine profile change has been observed during the shift from high (active disease) to low (after successful therapy) antigen load.

Accordingly, the present invention provides:
a method for assessing an intracellular pathogen infection, said method comprising:

(i) contacting a T-cell containing sample from said individual with an intracellular pathogen antigen;
(ii) detecting any cells that secrete IFN-γ and/or IL-2;
(iii) determining whether the sample comprises:
 (a) cells that secrete IFN-γ only;
 (b) cells that secrete IL-2 only; and/or
 (c) cells that secrete both IFN-γ and IL-2,
wherein the profile of (a), (b) and (c) indicates the status of the infection;
a method of monitoring an intracellular pathogen infection in an individual, comprising determining whether the individual has T-cells that secrete (a) IFN-γ only, (b) IL-2 only or (c) both IFN-γ and IL-2 in response to an intracellular pathogen antigen and optionally also determining any change in this cytokine profile; and
a kit for use in a method according to any one of the preceding claims comprising means for detecting cells that secrete IFN-γ, IL-2 or both IFN-γ and IL-2 in response to an intracellular pathogen antigen.

BRIEF DESCRIPTION OF THE SEQUENCES

Figure 1A:
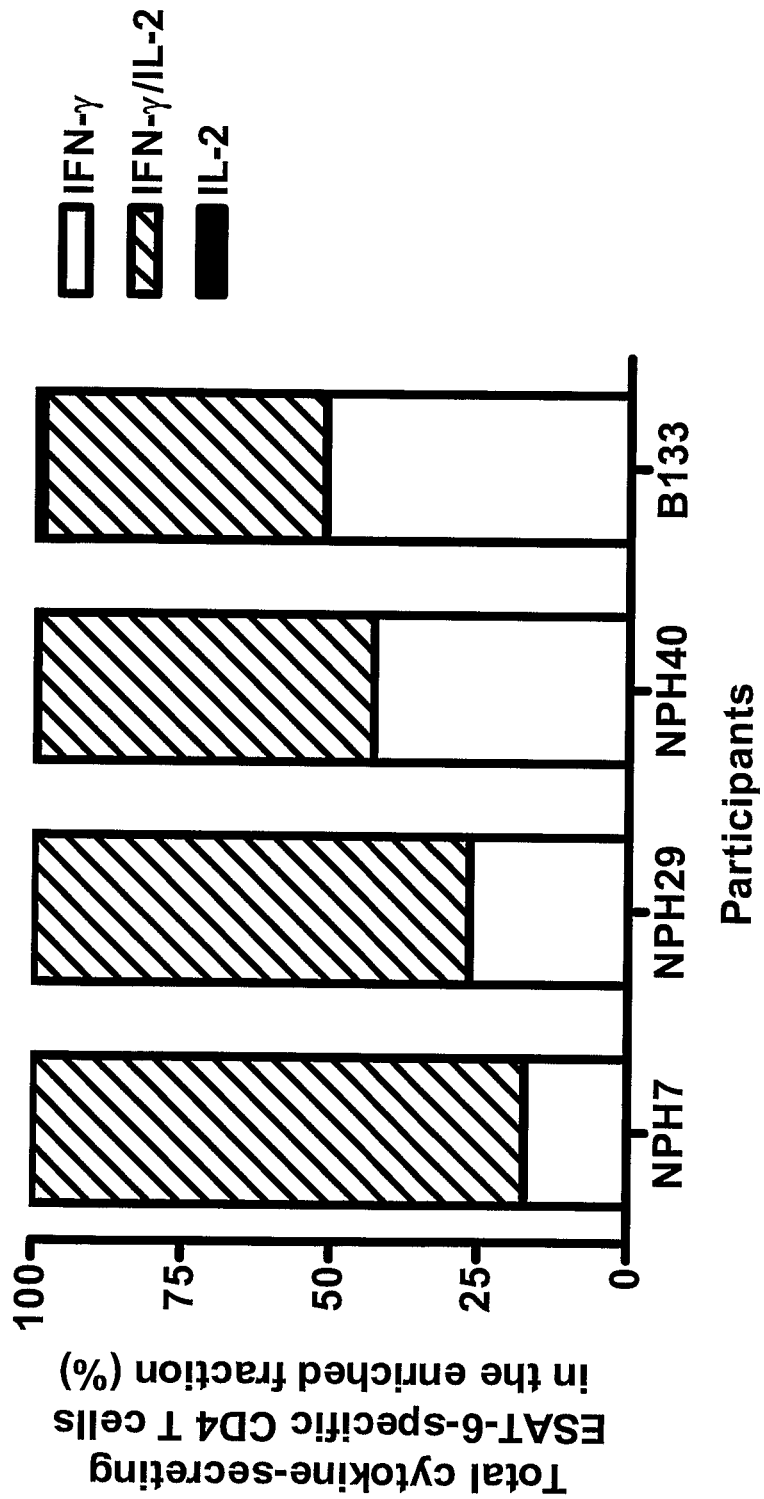
FIG. 1 shows the IFN-γ and IL-2 cytokine profile of CD4+ T cells in active tuberculosis and during and after anti-tuberculosis therapy. The percentages shown indicate the relative proportions of CD4+ cells producing IFN-γ and IL-2 in the enriched fraction with background levels of non-specific cytokine production subtracted. ESAT-6 and CFP-10-specific IFN-γ and IFN-γ/IL-2-secreting CD4+ T cells co-dominate in active tuberculosis, in whom bacterial load is high (A, B), whilst IFN-γ/IL-2-secreting T cells predominate during and after treatment which eradicated viable bacilli in vivo, with the loss of IFN-γ only secreting CD4+ T cells and the appearance of IL-2-secreting CD4+ T cells (C, D). This data was reproducibly observed in 4 active tuberculosis cases and in 9 follow-up samples from 5 patients 3 months into treatment and thereafter
Figure 1B:
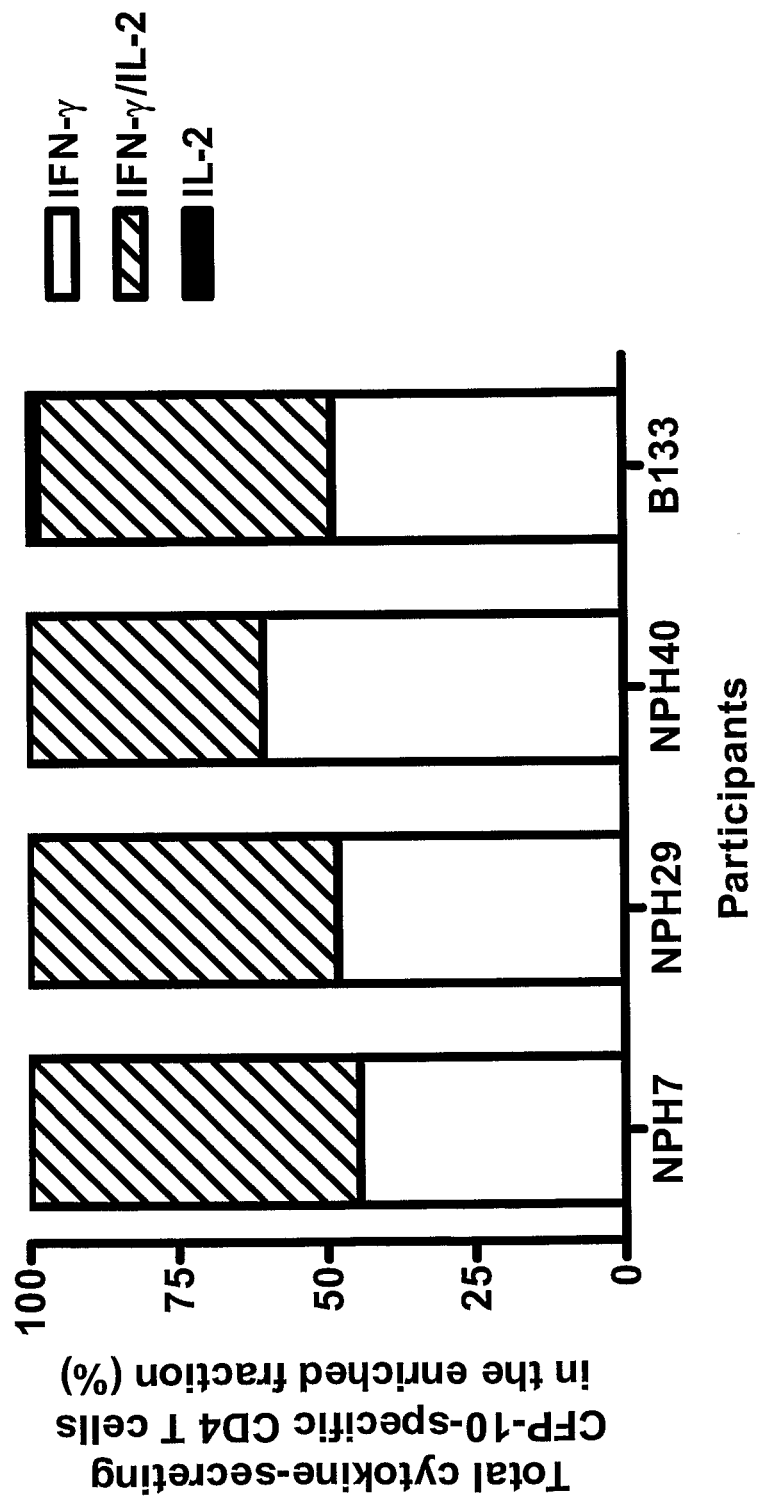
Figure 1C:
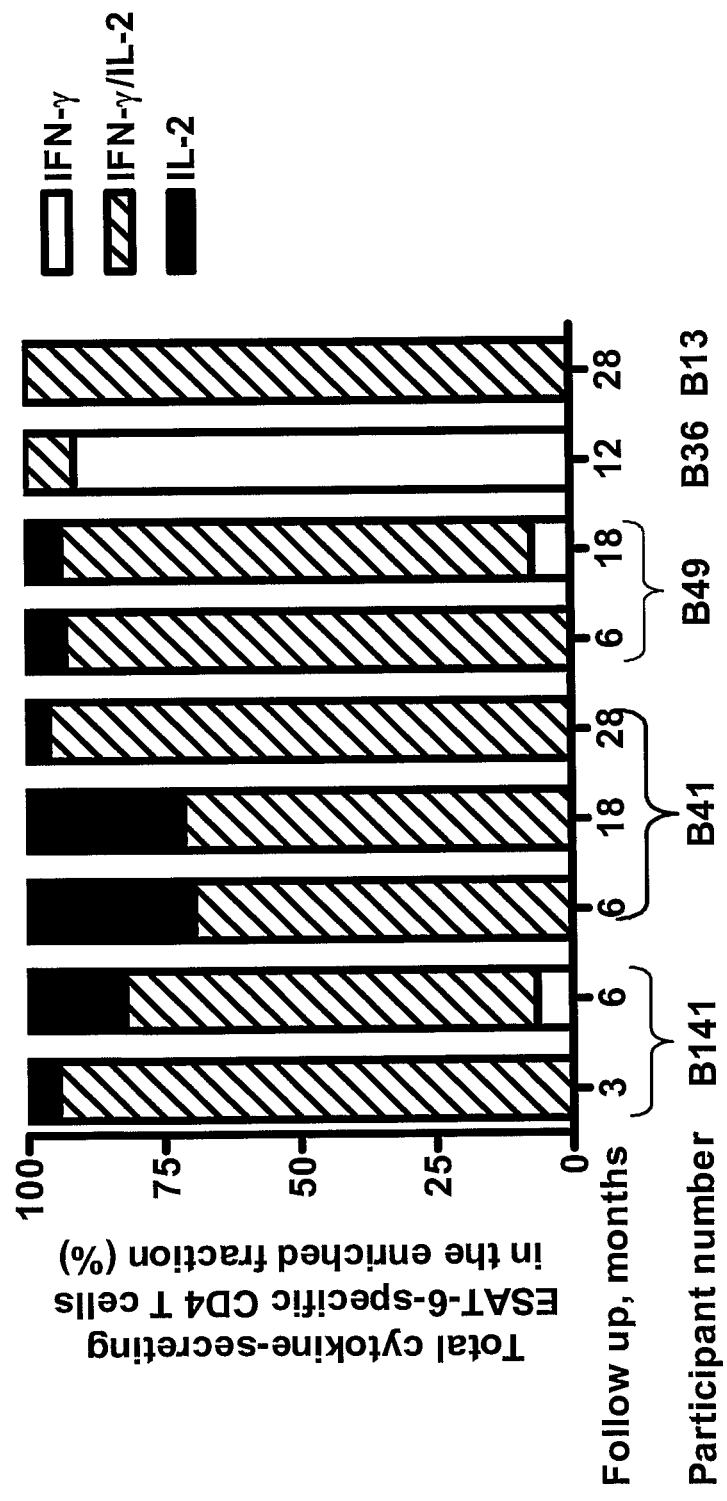
Figure 1D:
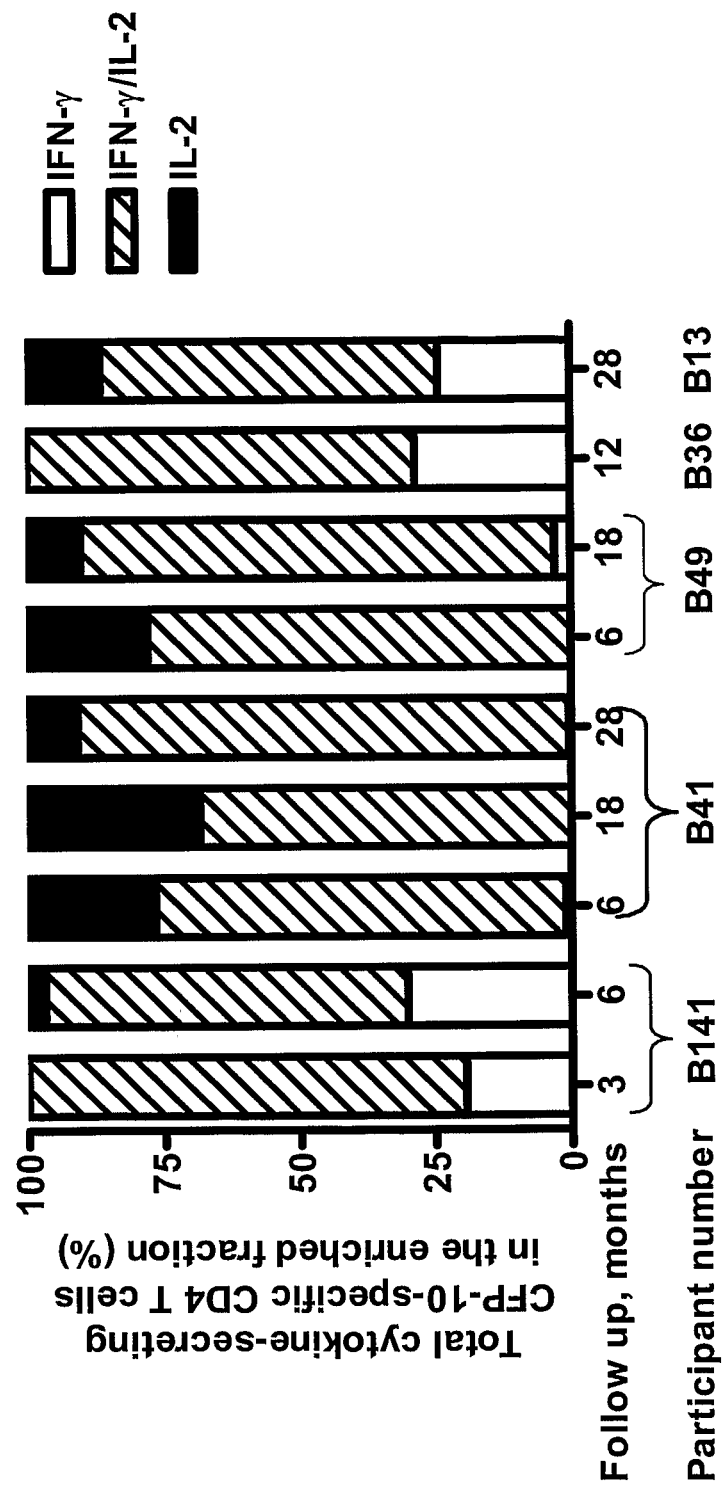

SEQ ID NO: 1 is the amino acid sequence of the Mycobacterium tuberculosis antigen ESAT-6.
SEQ ID NO: 2 is the amino acid sequence of the *Mycobacterium tuberculosis* antigen CFP-10.

DETAILED DESCRIPTION OF THE INVENTION

The invention provides a method of assessing an intracellular pathogen infection and/or monitoring an intracellular pathogen infection in an individual, comprising determining whether the individual has (a) T-cells that secrete IFN-γ only, (b) T-cells that secrete IL-2 only or (c) T-cells that secrete both IFN-γ and IL-2 in response to an intracellular pathogen antigen and optionally determining any change in this cytokine profile.

The intracellular pathogen may be a virus, bacterium or parasite. The virus is typically CMV, hepatitis A, hepatitis C, EBV or HSV. The pathogen may be Leishmania, *M. leprae*, or Listeria. In a preferred embodiment the infection is a mycobacterial infection, such as *Mycobacterium tuberculosis*.

The method may be used to determine the pathogen load, predict development and/or reactivation of disease, monitor anti-pathogen therapy, evaluate the efficacy of anti-pathogen drugs or vaccines or to determine whether anti-pathogen therapy results in a sterilising cure. For example, the method may be used to determine and/or monitor whether a patient has an active infection, latent infection, infection or disease which has spontaneously cleared or is clearing, infection or disease which has cleared or is clearing without medical intervention, or infection or disease which has been or is being cured.

A method of the invention typically comprises:
(i) contacting a T-cell containing sample from said individual with an intracellular pathogen antigen;
(ii) detecting any cells that secrete IFN-γ and/or IL-2;
(iii) determining whether the sample comprises:
  (a) cells that secrete IFN-γ only;
  (b) cells that secrete IL-2 only; and/or
  (c) cells that secrete both IFN-γ and IL-2.

The profile of (a), (b) and (c) indicates the status of the infection.

In one embodiment, the invention provides a method for determining pathogen load in an individual, wherein the presence and/or proportion of (a) is positively correlated with pathogen load and the presence and/or proportion of (b) is negatively correlated with pathogen load.

The individual is typically a mammal, preferably a human. The human may have an active or latent mycobacterial infection, or may have had such an infection recently. The human may test positive or negative in a Mantoux test. The human may be at risk of infection (such as mycobacterial infection), typically for socio-economic reasons or may have a genetic or acquired predisposition to the infection.

The mycobacterial infection may be caused by any mycobacteria. Preferably the mycobacterial infection is caused by *Mycobacterium tuberculosis*.

The human may be a known or suspected contact who has been exposed to or may have been exposed to *Mycobacterium tuberculosis*. Typically the exposure is to pulmonary tuberculosis, such as 'open' pulmonary tuberculosis which is sputum A.F.B. (acid-fast bacillus) smear positive. The contact may be someone whose exposure is a household, work place (such as a health care worker) or prison exposure (such as a prisoner). The exposure may have resulted from residing in a country with high prevalence of TB, and diagnostic testing after emigration to a country with a low prevalence of TB. Thus the contact may be an immigrant.

The human (for example who has a known or suspected recent or remote exposure) may be healthy, might have a co-infection or chronic condition or be on therapeutic agents putting them at a higher risk of developing active TB and/or which may make TB infection harder to diagnose. Examples include HIV infected individuals, individuals taking immunosuppressants (e.g. corticosteroids, azathioprine and anti-TNF-α agents, such as infliximab, and cancer therapy), hemodialysis patients, organ transplant recipients, diabetics and very young children (aged under 5 years old, particularly under 2 years old).

The T-cells which recognise the antigen in the method are generally T-cells which have been pre-sensitised in vivo to antigen from the pathogen. These antigen-experienced T-cells are generally present in the peripheral blood of a host which has been exposed to the pathogen at a frequency of 1 in $10^6$ to 1 in $10^3$ peripheral blood mononuclear cells (PBMCs). The T-cells may be CD4 and/or CD8 T-cells.

In the method the T-cells can be contacted with the antigen in vitro or in vivo, preferably in vitro in a sample from the individual.

Generally the T-cells which are contacted in the method are taken from the host in a blood sample, although other types of samples which contain T-cells can be used. The sample may be added directly to the assay or may be processed first. Typically the processing may comprise diluting of the sample, for example with water, buffer or media. Typically the sample is diluted from 1.5 to 100 fold, for example 2 to 50 or 5 to 10 fold.

The processing may comprise separation of components of the sample. Typically mononuclear cells (MCs) are separated from the samples. The MCs will comprise the T-cells and antigen presenting cells (APCs). Thus in the method the APCs present in the separated MCs can present the peptide to the T-cells. In another embodiment only T-cells, such as only CD4 T-cells, can be purified from the sample. PBMCs, MCs and T-cells can be separated from the sample using techniques known in the art, such as those described in Lalvani et al (1997) *J. Exp. Med.* 186, p 859-865.

Preferably the T-cells used in the assay are in the form of unprocessed or diluted samples, are freshly isolated T-cells (such as in the form of freshly isolated MCs or PBMCs) which are used directly ex vivo, i.e. they are not cultured before being used in the method or are thawed cells. However the T-cells can be cultured before use, for example in the presence of the antigen, and generally also exogenous growth promoting cytokines. During culturing the antigen is typically present on the surface of APCs, such as the APC used in the method. Pre-culturing of the T-cells may lead to an increase in the sensitivity of the method. Thus the T-cells can be converted into cell lines, such as short term cell lines (for example as described in Ota et al (1990) Nature 346, p 183-187).

The APC which is typically present in the method may come from the same host as the T-cell or from a different host. The APC may be a naturally occurring APC or an artificial APC. The APC is a cell which is capable of presenting the antigen to a T-cell. It is typically a B-cell, dendritic cell or macrophage. It is typically separated from the same sample as the T-cell and is typically co-purified with the T-cell. Thus the APC may be present in MCs or PBMCs. The APC is typically a freshly isolated ex vivo cell or a cultured cell. It may be in the form of a cell line, such as a short term or immortalised cell line. The APC may express empty MHC class II molecules on its surface.

In one embodiment the antigen is added to an assay comprising T-cells and APCs. For example, the antigen may be coated on an inner aspect of the container e.g. a tube into which the blood is drawn from the patient; alternatively, the antigen may be added to a container that already contains the T-cells and APCs. As discussed above the T-cells and APCs in such an assay could be in the form of MCs. When an antigen is used which can be recognised by the T-cell without the need for presentation by APCs then APCs are not required. Analogues which mimic the original antigen bound to a MHC molecule are an example of such an antigen.

In one embodiment the antigen is provided to the APC in the absence of the T-cell. The APC is then provided to the T-cell, typically after being allowed to present the antigen on its surface. The antigen may have been taken up inside the APC and presented, or simply be taken up onto the surface without entering inside the APC.

Typically $10^5$ to $10^7$, preferably $2.5 \times 10^5$ to 106 PBMCs are added to each assay. In the case where peptide is added directly to the assay its concentration is from $10^{-1}$ to $10^3$ μg/ml, preferably 0.5 to 50 μg/ml or 1 to 10 μg/ml.

Typically the length of time for which the T cells are incubated with the antigen is from 4 to 24 hours (preferably 5 to 18 hours) for effector T-cells or for more than 24 hours for central memory cells. When using ex vivo PBMCs it has been found that $5.0 \times 10^6$ PBMCs can be incubated in 10 μg/ml of peptide for 5 hours at 37° C.

Any suitable antigen may be used in a method of the invention. Typically the antigen is a mycobacterial or *M. tuberculosis* antigen. The antigen may be in the form of a naturally occurring protein which is recognised by a T-cell. Suitable *M. tuberculosis* antigens include ESAT-6 and CFP-10. The amino acid sequences of these antigens are shown in SEQ ID NOs: 1 and 2, respectively.

The antigen may be a fragment (such as a peptide) and/or homologue of a naturally occurring protein which is recognised by a T-cell that recognises the natural T-cell epitope sequence. The antigen may also be an analogue which mimics the epitope of the naturally occurring protein bound to a MHC molecule.

IL-2 or IFN-γ can typically be detected by allowing them to bind to a specific capture agent which may be immobilised on a support such as a plate, bead or the cytokine-secreting cell itself, and then measuring the presence of the specific binding agent/IL-2 complex and/or the specific binding agent/IFN-γ complex typically with a second binding detection agent. A washing step can be incorporated to remove material which is not specifically bound to the capture agent.

Typically the second agent binds IFN-γ or IL-2 at a site which is different from the site which binds the first agent. The second agent may be directly conjugated to an enzyme such as alkaline phosphatase, or fluorescent label or may comprise a biotin moiety to be detected by a third agent comprising strepavidin, which is directly conjugated to an enzyme or fluorescent label. The conjugated enzyme then changes colour of a reagent. The agent is preferably an antibody, mono- or polyclonal. Antibodies to IL-2 and IFN-γ are commercially available, or can be made using standard techniques.

The preferred method employed to detect EFN-γ and/or IL-2 will be based on sandwich immunoassays detecting the frequency of cytokine-secreting cells such as colour or fluorescent ELISpot, limited dilution assays, intracellular cytokine staining and cytokine secretion assays with or without enrichment of cytokine-secreting cells as pioneered by Miltenyi Biotec. Alternatively, the amount of cytokine secreted can be measured for example by an ELISA based system such as the whole blood QUANTIFERON® (tuberculosis test) system with the capture antibody immobilised on a plate, and its modifications (for example as available from Cellestis) or LUMINEX® (corporation with products that measure multiple analytes simultaneously) suspension array technology using BEADLYTE® (beads that are internally dye-labeled and contain surface Carboxyl groups for covalent attachment of ligands) kits with the capture antibody immobilised on a bead. Cytokine mRNA expression can also be measured with assays such as RT-PCR.

In one embodiment the detection system which is used is the ex-vivo ELISpot assay described in WO 98/23960. In that assay IFN-γ secreted from the T-cell is bound by a first IFN-γ specific antibody which is immobilised on a solid support. The bound IFN-γ is then detected using a second IFN-γ specific antibody which is labelled with a detectable label. Such a labelled antibody can be obtained from MABTECH (Stockholm, Sweden). Other detectable labels which can be used are discussed below.

The methods of the invention allow the determination of whether pathogen antigen-responsive T-cells that produce IFN-γ, IL-2 or both IFN-γ and IL-2 are each present in an individual. The relative amounts of each type of antigen-responsive T-cell may also be determined. The presence or absence of each type of T-cell enables the state of the infection in the individual and/or the mycobacterial load to be determined.

The presence of IFN-γ only secreting cells and cells which secrete both IFN-γ and IL-2 occurs during states of high antigen load. During states of low antigen load, antigen-specific T-cells stop secreting IFN-γ only, predominantly secrete both IFN-γ and IL-2 and newly secrete IL-2 only. Thus, IFN-γ only secreting cells are positively correlated with antigen load and IFN-γ/IL-2 secreting cells are negatively correlated with antigen load. The profile of the three types of antigen-responsive T-cells may be used to determine pathogen load in the individual.

Where the individual has a latent mycobacterial infection, but is not showing disease symptoms assessing and/or monitoring the profile of IFN-γ, IL-2 and IL-2/IFN-γ secreting cells will be predictive of the risk of reactivation. The presence of cells secreting IFN-γ only or IFN-γ/IL-2 typically indicates that the individual has a latent infection associated with a risk of progression to active tuberculosis. The number or proportion of cells secreting IFN-γ only may positively correlate with the risk of progression or reactivation, which is also strongly influenced by several host factors including for example, but not limited to, age, concomitant illness, HIV co-infection, iatrogenic immunosuppression and how recent the infection is. Conversely, the number or proportion of cells secreting IL-2 only, with or without the presence of cells secreting IFN-γ and IL-2, may inversely correlate with the risk of progression or reactivation and a relatively high number of IL-2-secreting cells may indicate a very low risk of reactivation.

The method may be used to monitor the progress of anti-pathogen (preferably mycobacterium) therapy in active or latent infection in an individual. A decrease in the number of (or relative amount of) IFN-γ only secreting cells and/or an increase in the number of (or relative amount of) IL-2 secreting cells indicates that the therapy is effective. Similarly, an increase in the predominance of cells that secrete both IFN-γ and IL-2 is an indication that the therapy is working.

The method may be used to evaluate the efficacy of known anti-pathogen drugs or vaccines or to test the efficacy of potential new anti-pathogen drugs or vaccines. In an individual having a pathogen infection, a decrease in the number of (or relative amount of) IFN-γ only secreting cells and/or an increase in the number of (or relative amount of) IL-2 secreting cells indicates that the therapy is efficacious. Similarly, an increase in the predominance of cells that secrete both IFN-γ and IL-2 is also a positive indication of efficacy.

In testing a vaccine, the profile of the three antigen-responsive cell types may be examined following infection to determine the effectiveness of the vaccine. Typically, a profile associated with low pathogen load indicates that the vaccine is effective and a profile associated with high pathogen load is less promising.

Thus, the individual tested in a method of the invention may have received an anti-pathogen drug or vaccine. In this embodiment, the method may further comprise comparing the status of said infection to the previously determined status of said infection in said individual, thereby monitoring the effectiveness of said anti-pathogen drug or vaccine in said individual.

Alternatively, the individual may have received a test anti-pathogen drug or vaccine. In this embodiment, the method may further comprise comparing the status of said infection to the previously determined status of said infection in said individual, thereby determining the efficacy of said test drug or vaccine.

The invention also provides a kit for carrying out the methods of the invention comprising means for detecting cells that secrete IFN-γ, IL-2 or both IFN-γ and IL-2 in response to a pathogen (preferably mycobacterial) antigen. The kit may optionally include instructions for correlating the profile of IFN-γ, IL-2 and/or IFN-γ and IL-2 secreting cells to the status of the infection. For example, the instructions may be for correlating the detection of IFN-γ, IL-2 and/or IFN-γ and IL-2 secreting cells to the pathogen load.

Typically the means to detect recognition allows or aids detection based on the techniques discussed above. Thus, the means may allow detection of IFN-γ and IL-2 secreted by the T-cells after recognition. The kit may thus additionally include a specific binding agent for each of IFN-γ and IL-2, such as an antibody. The agent is typically immobilised on a solid support. This means that after binding the agent the IFN-γ and/or IL-2 will remain in the vicinity of the T-cell that secreted it. Thus 'spots' of IFN-γ/agent and/or IL-2/agent complex are formed on the support, each spot representing a T-cell which is secreting IFN-γ and/or IL-2. Quantifying the spots, and typically comparing against a control, allows determination of the relative numbers of cells that secrete IFN-γ, IL-2 or both IFN-γ and IL-2.

The kit may also comprise a means to detect the IFN-γ/agent and/or IL-2/agent complexes. A detectable change may occur in the agent itself after binding IFN-γ and/or IL-2, such as a colour change. Alternatively a second agent directly or indirectly labelled for detection may be allowed to bind the IFN-γ/agent and/or IL-2/agent complex to allow the determination of the spots. As discussed above the second agent may be specific for IFN-γ or IL-2, but binds a different site on IFN-γ or IL-2 than the first agent.

The immobilised support may be a plate with wells, such as a microtitre plate. Each assay can therefore be carried out in a separate well in the plate.

The kit may additionally comprise medium for the T-cells, detection agents or washing buffers to be used in the detection steps. The kit may additionally comprise reagents suitable for the separation from the sample, such as the separation of PBMCs or T-cells from the sample. The kit may be designed to allow detection of the T-cells directly in the sample without requiring any separation of the components of the sample.

The kit may also comprise controls, such as positive or negative controls. The positive control may allow the detection system to be tested. Thus the positive control typically mimics recognition of the peptide in any of the above methods. Typically in the kits designed to determine recognition in vitro the positive control is IFN-γ and/or IL-2.

The kit may also comprise a means to take a sample containing T-cells from the human, such as a blood sample. The kit may comprise a means to separate mononuclear cells or T cells from a sample from the individual.

The following Examples illustrate the invention.

EXAMPLES

Example 1

IFN-γ and IL-2 Cytokine Profile of CD4+ T Cells in Active Tuberculosis and During and After Anti-Tuberculosis Therapy Frozen PBMC were stimulated with *M. tuberculosis*-specific ESAT-6 or CFP-10 peptide pools (15-mers overlapping by 10 amino-acids) for 5 h at 37° C. Secreted IFN-γ and IL-2 was then caught on the surface of the secreting cell for 45 min at 37° C. followed by enrichment for IFN-γ and IL-2-positive cells with the IFN-γ (APC) and IL-2 (PE) cell enrichment and detection kits according to the manufacturer (Miltenyi Biotec Ltd). PBMCs were stained with anti-CD4, anti-IFN-γ, anti-IL-2 antibodies, and PerCP-conjugated anti-CD14, PerCP-conjugated anti-CD19 antibodies to exclude monocytes and B cells respectively, and Via-Probe to exclude dead cells. Plots were gated on CD4+ CD14− CD19− Via-Probe-cells.

The results are shown in FIG. 1. ESAT-6 and CFP-10-specific IFN-γ and IFN-γ/IL-2-secreting CD4+ T-cells co-dominated in individuals with active tuberculosis, in whom bacterial load is high (FIGS. 1A and B). In contrast, IFN-γ/IL-2-secreting T-cells predominated during and after treatment which eradicated viable bacilli in vivo, with the loss of IFN-γ only secreting CD4+ T cells and the appearance of IL-2-secreting CD4+ T cells (FIGS. 1C and D). This data was reproducibly observed in 4 active tuberculosis cases and in 9 follow-up samples from 5 patients 3 months into treatment and thereafter.

Figure 2A:
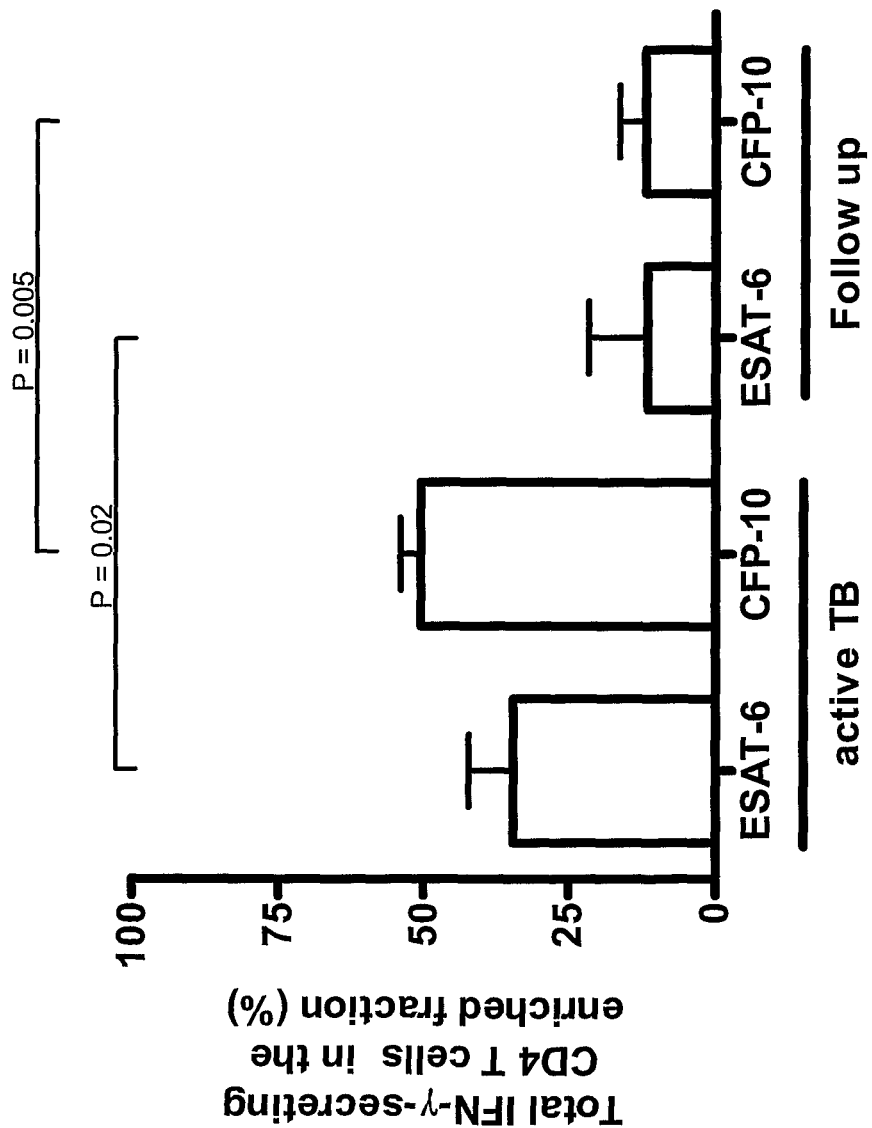
FIG. 2 shows the proportion and frequency of ESAT-6 and CFP-10-specific CD4+ T cell IFN-γ (white bars/symbols), IFN-γ/IL-2 (grey bars/symbols) and IL-2 (black bars/symbols) responses in active TB compared to follow up time points (during and after treatment). The proportion of ESAT-6 and CFP-10-specific CD4+ T cells secreting IFN-γ and/or IL-2 in the enriched fraction (A) and frequencies of these cells as determined after magnetic enrichment of IFN-γ and IL-2-secreting cells (B) are shown. The horizontal lines indicate the median positive response. The P values indicate whether there is a statistical difference between active TB and follow up.
Figure 2B:
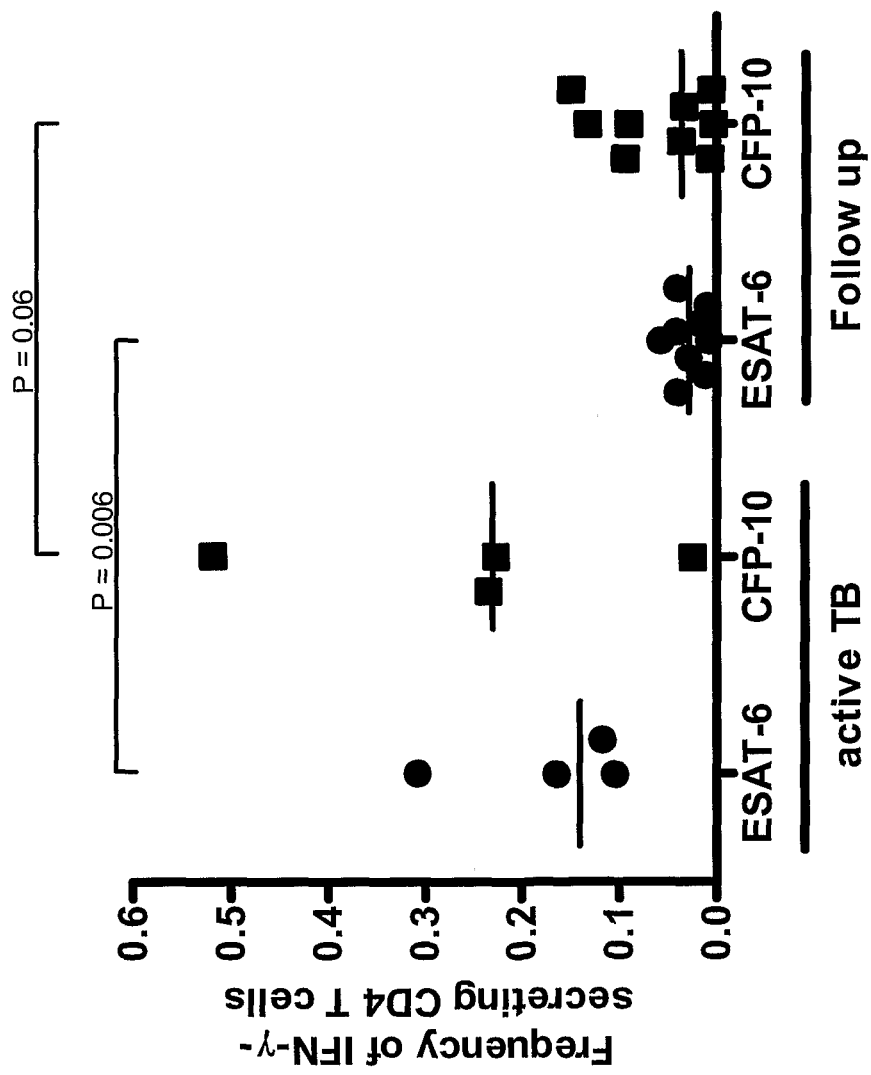
Figure 3A:
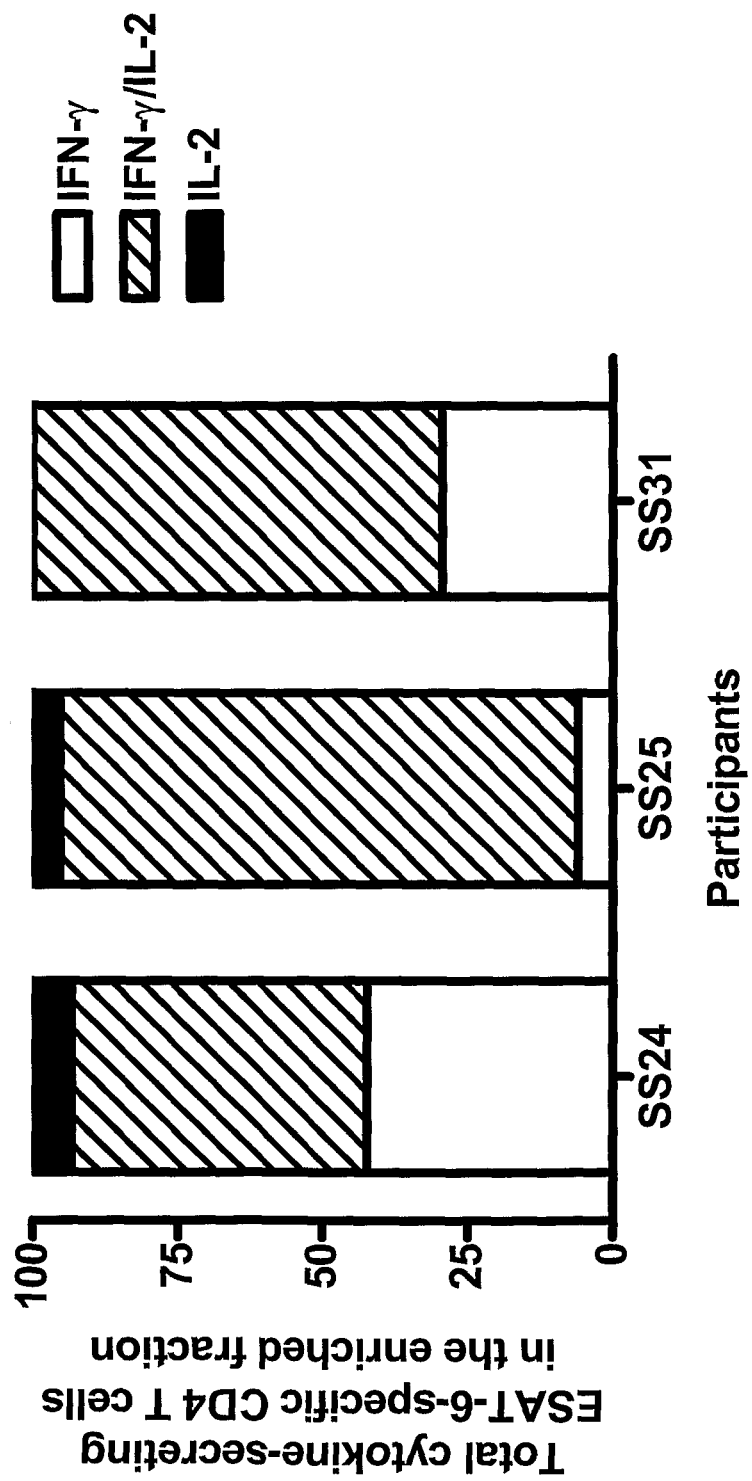
FIG. 3 shows the IFN-γ and IL-2 cytokine profile of CD4+ T cells in self-healed tuberculosis. PBMC were stimulated with ESAT-6 and CFP-10 and enriched for IFN-γ and IL-2-secreting cells as for FIG. 1. IFN-γ, IFN-γ/IL-2 and IL-2-secreting CD4+ T cells were observed in self-healed participants in whom viable bacilli persist.
Figure 3B:
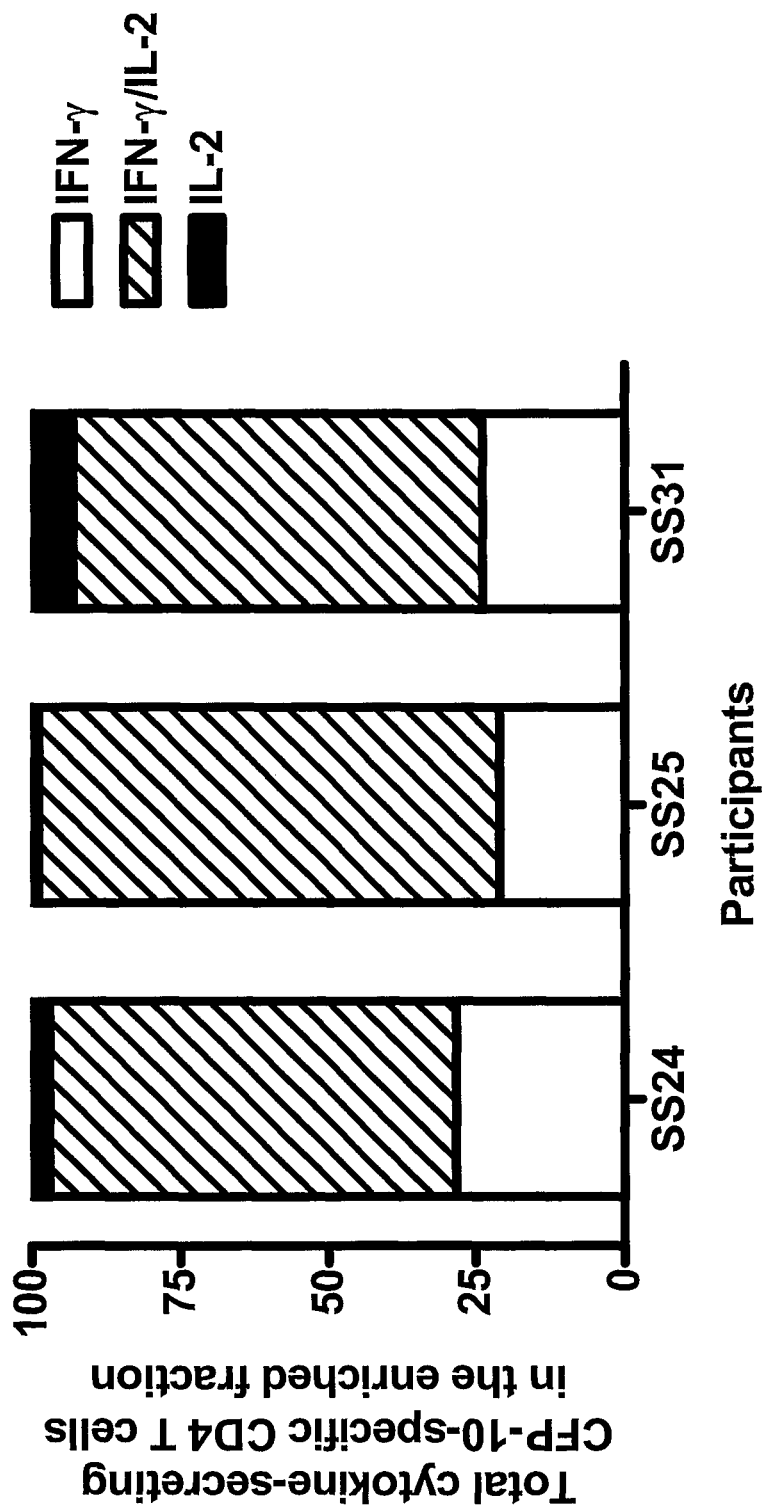
Figure 4:
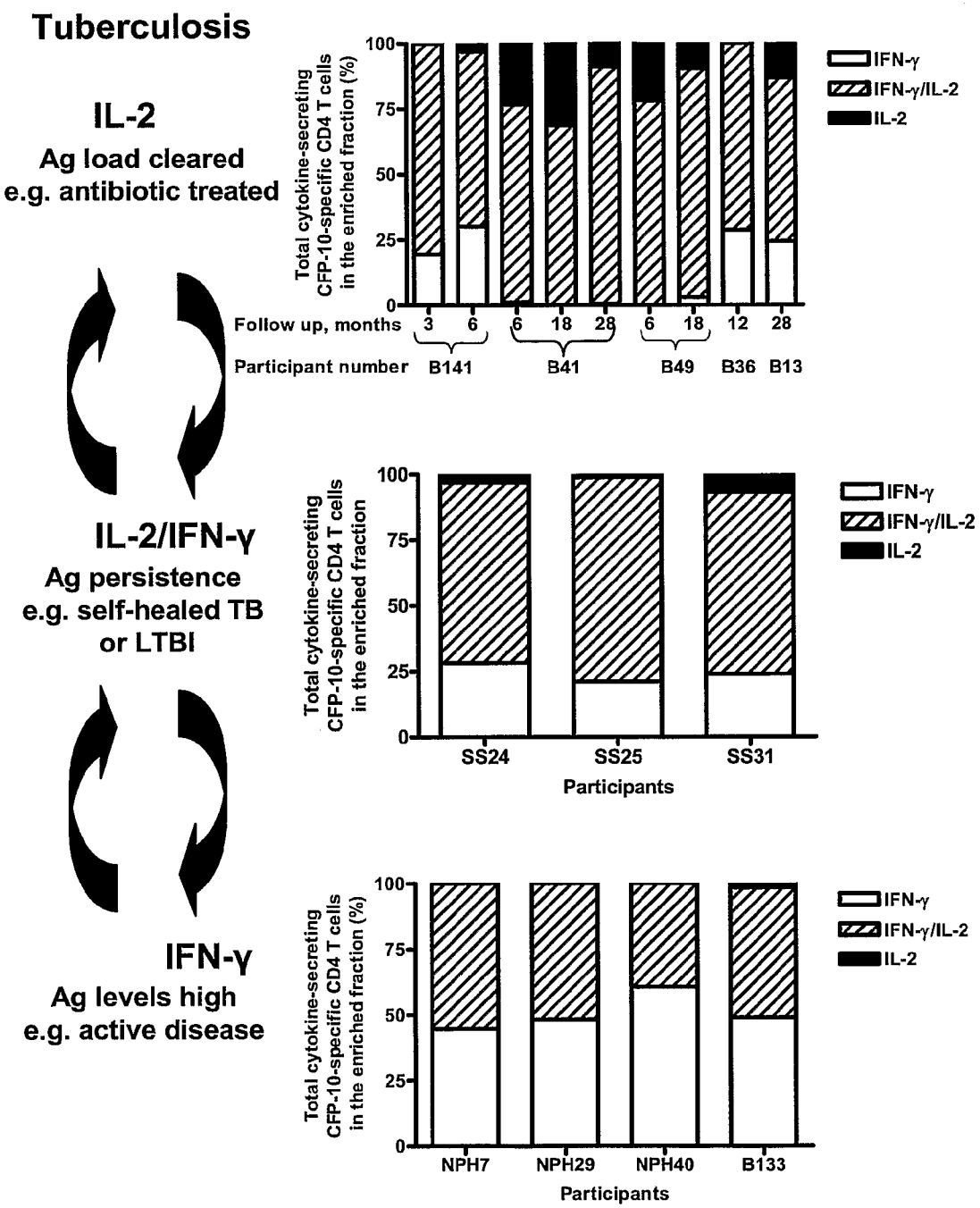
FIG. 4 summarises the observed cytokine profiles in different outcomes of tuberculosis infection.
Figure 5:
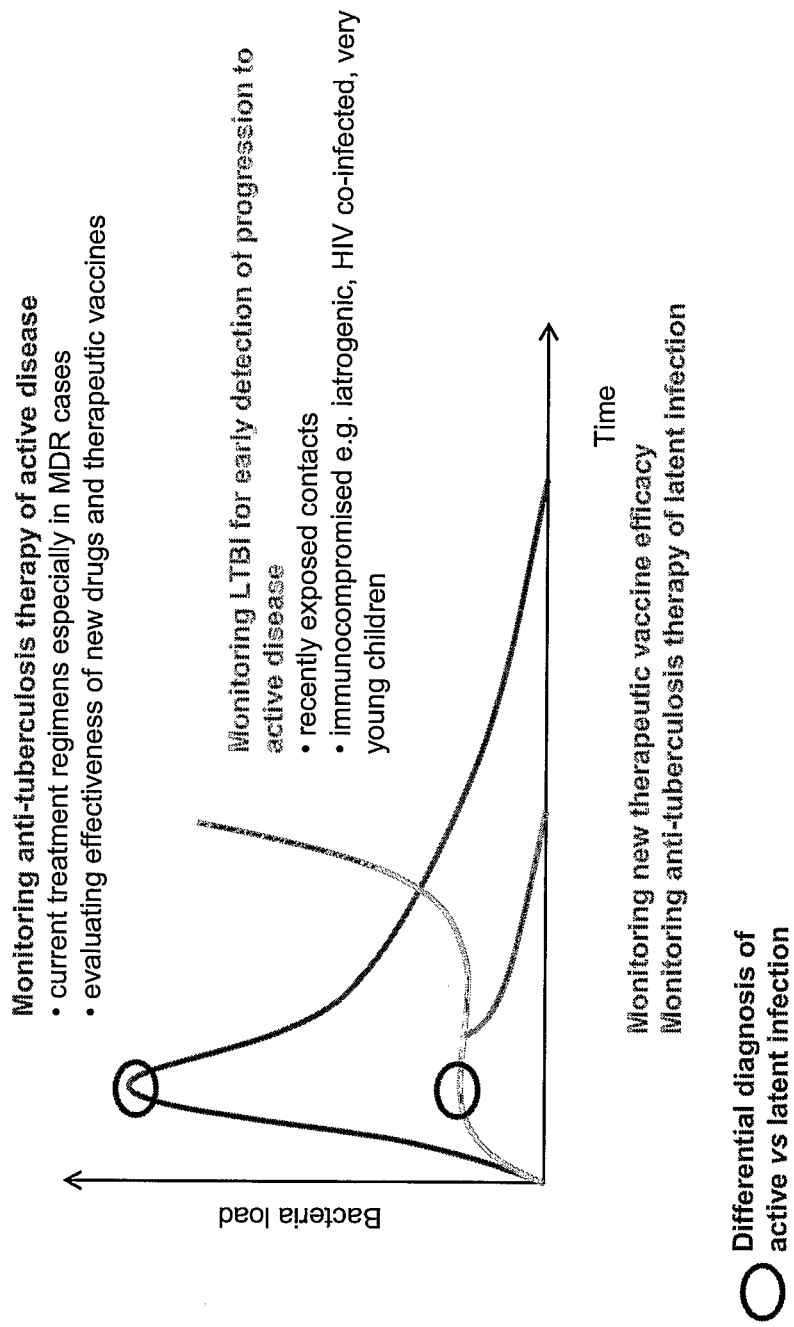
FIG. 5 shows potential applications of this invention.

The same results are also shown in FIG. 2 where the relative proportions and frequencies of ESAT-6 and CFP-10-specific IFN-γ, IFN-γ/IL-2 and IL-2-secreting CD4+ T cells between samples from active tuberculosis patients before initiation of treatment with samples after initiation of treatment are compared. The relative proportion and likewise the absolute frequency of ESAT-6 and CFP-10-specific IFN-γ-only secreting CD4+ T cells were higher in untreated active tuberculosis compared to follow up during and after treatment whilst the relative proportion of ESAT-6 and CFP-10-specific IL-2-only secreting CD4+ T cells were higher during follow up compared to untreated active tuberculosis.

Example 2

IFN-γ and IL-2 Cytokine Profile of CD4+ T Cells in Self-Healed Tuberculosis

PBMC were stimulated with ESAT-6 and CFP-10 and enriched for IFN-γ and IL-2-secreting cells as described in Example 1. IFN-γ, IFN-γ/IL-2 and IL-2-secreting CD4+ T cells were observed in self-healed participants in whom viable bacilli persist. The self-healed participants are an at-risk group of reactivation of disease.

The invention claimed is:

1. A method for assessing and/or monitoring a *Mycobacterium tuberculosis* infection in an individual, said method comprising:
(i) contacting a T-cell containing sample from said individual with a mycobacterial antigen, wherein the mycobacterial antigen is a peptide which is recognized by a T-cell and wherein the T-cell recognizes a natural T-cell epitope sequence in a naturally occurring *Mycobacterium tuberculosis* protein;
(ii) detecting any cells that secrete IFN-γ and/or IL-2'
(iii) determining:
  (a) whether the sample comprises cells that secrete IFN-γ only;
  (b) whether the sample comprises cells that secrete 11-2 only; and
  (c) whether the sample comprises cells that secrete both IFN-γ and IL-2,
(iv) inferring the mycobacterial load in the individual, wherein the proportion of (a) is positively correlated with mycobacterial load, the proportion of (b) is negatively correlated with mycobacterial load, and the proportion of (c) is negatively correlated with mycobacterial load;
wherein the profile of cells that secrete IFN-γ only, ells that secrete IL-2 only, and cells that secrete both IFN-γ and IL-2 indicates the status of the infection as follows:
(A) where an individual has recovered from tuberculosis, the likelihood of reactivation of the disease is positively correlated with (a) and negatively correlated with (b) and (c);
(B) where an individual has tuberculosis, untreated disease is positively correlated with (a) and negatively correlated with (b) and (c), whereas treated disease is positively correlated with (b) and (c) and negatively correlated with (a);
(C) where an individual has tuberculosis infection, active disease is positively correlated with (a) and negatively correlated with (b) and (c), whereas latent infection is positively correlated with (b) and (c) and negatively correlated with (a);
(D) where an individual has a latent tuberculosis infection but no disease symptoms, the risk of progression or reactivation of the infection is positively correlated with (a) and negatively correlated with (b) and (c), such as in recently exposed individuals;
(E) where an individual is being treated for tuberculosis infection, the success of the treatment correlates positively with (b) and (c) and negatively with (a).

2. A method according to claim 1(E), wherein said individual has received a drug or vaccine which treats said infection.

3. A method according to claim 2, further comprising comparing the status of said infection to the previously determined status of said infection in said individual, thereby monitoring the effectiveness of said drug or vaccine in said individual.

4. A method according to claim 1(E), wherein said individual has received a test drug or vaccine intended to treat said infection.

5. A method according to claim 4, further comprising comparing the status of said infection to the previously determined status of said infection in said individual, thereby determining the efficacy of said test drug or vaccine.

6. A method according to claim 1, wherein the individual is human or mammal.

7. A method according to claim 1, wherein said individual has active TB disease or latent tuberculosis infection (LTBI).

8. A method according to claim 1, wherein said individual is at risk of contracting said infection.

9. A method according to claim 1, wherein the antigen is ESAT-6 or CFP-10 or another mycobacterial antigen.

10. A method according to claim 1, wherein the antigen is a fragment or homologue of a naturally occurring *Mycobacterium tuberculosis* protein which is recognized by a T-cell which recognizes a natural T-cell epitope sequence in the protein.

11. A method according to claim 1, wherein (a), (b) and (c) are detected using immobilized antibodies to IFN-$\gamma$ and IL-2.

12. A method according to claim 1, wherein said sample comprises freshly isolated T-cells or T cells after being frozen.

13. A method according to claim 1, wherein said sample comprises T-cells that have been cultured in vitro.

14. A method according to claim 1 which is carried out to:
(i) predict development and/or reactivation of tuberculosis;
(ii) monitor anti-tuberculosis therapy;
(iii) evaluate the efficacy of an anti-tuberculosis drug or vaccine; or
(iv) determine whether anti-tuberculosis therapy results in a sterilising cure.

15. A method according to claim 1 wherein the individual is a small child and/or is immunocompromised.

16. A method according to claim 1 wherein the monitoring method defined in claim 14 is carried out at multiple time intervals to determine a change in status of the infection.

17. A method according to claim 16 wherein the monitoring method is carried out at least 3 to 20, preferably 6 to 10, times and/or is carried out at least every 40 days and/or for the duration of the period of risk of reactivation and/or is carried out to determine if latent tuberculosis is becoming active.

18. A method for assessing and/or monitoring a *Mycobacterium tuberculosis* infection in an individual, said method comprising:
(i) contacting a T-cell containing sample from said individual with a mycobacterial antigen;
(ii) detecting any cells that secrete IFN-$\gamma$ and/or IL-2;
(iii) determining:
(a) whether the sample comprises cells that secrete IFN-$\gamma$ only;
(b) whether the sample comprises cells that secrete IL-2 only; and
(c) whether the sample comprises cells that secrete both IFN-$\gamma$ and IL-2,
(iv) inferring the mycobacterial load in the individual, wherein the proportion of (a) is positively correlated with mycobacterial load, the proportion of (b) is negatively correlated with mycobacterial load, and the proportion of (c) is negatively correlated with mycobacterial load;
wherein the profile of cells that secrete IFN-$\gamma$ only, cells that secrete IL-2 only, and cells that secrete both IFN-$\gamma$ and IL-2 indicates the status of the infection as follows:
(A) where an individual has recovered from tuberculosis, the likelihood of reactivation of the disease is positively correlated with (a) and negatively correlated with (b) and (c);
(B) where an individual has tuberculosis, untreated disease is positively correlated with (a) and negatively correlated with (b) and (c), whereas treated disease is positively correlated with (b) and (c) and negatively correlated with (a);
(C) where an individual has not received treatment for tuberculosis infection, active disease is positively correlated with (a) and negatively correlated with (b) and (c), whereas latent infection is positively correlated with (b) and (c) and negatively correlated with (a);
(D) where an individual has a latent tuberculosis infection but no disease symptoms, the risk of progression or reactivation of the infection is positively correlated with (a) and negatively correlated with (b) and (c), such as in recently exposed individuals;
(E) where an individual is being treated for a tuberculosis infection, the success of the treatment correlates positively with (b) and (c) and negatively with (a),
wherein the antigen is a peptide of a naturally occurring *Mycobacterium tuberculosis* protein which is recognized by a T-cell which recognizes a natural T-cell epitope sequence in the protein.

* * * * *